United States Patent [19]
Johnson, Jr. et al.

[11] Patent Number: 5,413,004
[45] Date of Patent: May 9, 1995

[54] METHOD AND APPARATUS FOR SAMPLING COAL

[75] Inventors: George F. Johnson, Jr., Pikeville; Arnemann R. Gredner, Pippa Passes, both of Ky.

[73] Assignee: Johnson Industries, Inc., Pikeville, Ky.

[21] Appl. No.: 253,430

[22] Filed: Jun. 2, 1994

Related U.S. Application Data

[63] Continuation of Ser. No. 97,361, Jul. 23, 1993, abandoned.

[51] Int. Cl.⁶ ............................................. G01N 1/20
[52] U.S. Cl. .............................. 73/863.41; 73/864.43
[58] Field of Search ............... 73/863.41, 863.44, 863, 73/45, 863.51–863.56, 863.58, 864.31, 864.34, 864.41, 864.43–864.45, 864.73, 864.74

[56] References Cited

U.S. PATENT DOCUMENTS

| Re. 29,087 | 12/1976 | Larson | 73/864.31 |
|---|---|---|---|
| 1,860,107 | 5/1932 | Lien | 73/863.51 |
| 2,495,944 | 1/1950 | Pletta et al. | 73/863.53 |
| 2,664,189 | 12/1953 | Hager . | |
| 3,447,381 | 6/1969 | Langtry et al. | 73/864.43 |
| 3,690,179 | 9/1972 | Olson | 73/863.56 |
| 3,841,161 | 10/1974 | Huntington . | |
| 4,179,929 | 12/1979 | Redding . | |
| 4,215,579 | 8/1980 | Hines et al. | 73/863.53 |
| 4,345,484 | 8/1982 | Gould et al. . | |
| 5,211,062 | 5/1993 | Moser | 73/864.34 |

FOREIGN PATENT DOCUMENTS

| 1353605 | 5/1974 | United Kingdom | 73/863.56 |
|---|---|---|---|
| 0585428 | 12/1977 | U.S.S.R. | 73/863.54 |

*Primary Examiner*—Robert Raevis
*Attorney, Agent, or Firm*—Frost & Jacobs

[57] ABSTRACT

A coal sampling device is provided for the efficient extraction of a core sample of coal from a container, such as a coal truck or railroad hopper car, and crushing of the extracted coal sample into particles useful for laboratory analysis. Uncrushed pieces of extracted coal are transported to a separating device that allows most of these extracted coal pieces to fall back into the container through several open windows. The separating device also includes an additional window through which extracted coal pieces fall into a crushing device, where the coal pieces are crushed to pebble-sized pieces. The crushed coal pieces are allowed to fall out of the bottom of the coal crushing device, and a portion of the crushed pieces are collected by a sample collecting receptacle, which accumulates portions of the crushed coal throughout the core extraction process so that a true representative sample of the total extracted core is collected. During or at the end of the extraction/sampling process, the crushed coal sample is removed from the receptacle by a vacuum or air pressure which is provided to propel the crushed coal pieces through a hose or pipe that directs the crushed coal sample to a laboratory or collecting work station.

17 Claims, 3 Drawing Sheets

METHOD AND APPARATUS FOR SAMPLING COAL

This is a continuation of application Ser. No. 08/097,361, filed Jul. 23, 1993, now abandoned.

TECHNICAL FIELD

The present invention relates generally to coal sampling devices used with transport equipment and is particularly directed to an auger-type coal extraction device of the type which crushes the extracted coal into pieces small enough for laboratory analysis. The invention is specifically disclosed as a boom-mounted or portable coal sampling device which first extracts coal from a truck or railroad car, then separates the uncrushed coal into several portions, whereby most of the portions are not further sampled or crushed, and only a minor portion is crushed, then sampled further until a useful amount is accumulated for laboratory analysis.

BACKGROUND OF THE INVENTION

Existing coal sampling devices tend to be large in size and stationary in nature. Typical coal sampling devices are mounted to a building's structural steel, and require between two and five floors of vertical space for their operation. An example of such a coal sampling device is given in U.S. Pat. No. 3,841,161, which discloses a sampler that is located above moving railroad hopper cars. This sampling device is movable on a conveyer so that it can travel along with the moving hopper cars long enough to obtain a large sample. This sampling device is permanently mounted to the structural steel of a building, and requires at least two or three floors of vertical space.

Another coal sampling device is disclosed in U.S. Pat. No. 4,179,929 (by Redding) in which a stationary coal sampling device drills vertically into a coal sample sitting in a truck to extract a core sample. The Redding device is quite large in that it requires five or six floors of vertical space for its operation.

Existing coal sampling devices also extract and crush a very large amount of coal, when only a small final sample is desired for analysis by a laboratory station. For example, the Redding coal sampling device crushes the entire sample that has been extracted from the coal truck. A portion of the coal is separated for analysis only after the entire core sample has been crushed. Since the entire sample is crushed, a very large coal crushing device is required, along with an associated, relatively large horsepower motor, to quickly and adequately crush the entire core sample. Since only a portion of the sample is ultimately required for laboratory analysis, this is a significant waste of electrical energy, as well as needlessly making the equipment much larger than necessary.

In addition, existing coal sampling devices are configured such that only their auger is placed over the coal truck or coal bin. The crusher and final sampling device are located elsewhere, and require a conveyor to transport the coal both to and from the crusher. Furthermore, the "rejected" coal not used in the final sample must also be conveyed back to the truck or to some other storage container.

SUMMARY OF THE INVENTION

Accordingly, it is a primary object of the present invention to provide a coal sampling device that extracts a large sample of coal from a container, randomly separates the extracted coal, then crushes only a small portion of that extracted coal for later use in laboratory analysis.

It is another object of the present invention to provide a coal sampling device which is small enough in physical size to as to be portable, such that it need not be permanently mounted to the structural steel of a particular building.

It is a further object of the present invention to provide a coal sampling device which is more efficient and uses less energy during its operation than existing coal sampling devices by crushing only a small portion of extracted coal and retaining only a yet smaller sample of crushed coal for later use in laboratory analysis.

It is yet another object of the present invention to provide a coal sampling device which can be located at the end of the boom of a hydraulic lift of a configuration in which the entire core extractor, separator, coal crusher, and final sample collecting device are all supported in one self-contained package which is shiftable at the end of the boom.

It is still another object of the present invention to provide a coal sampling device which will return all the coal, with the exception of a small final sample of about 1–2 lbs., directly back into the container from which it was sampled.

It is yet another object of the present invention to provide a coal sampling device which requires no mechanical conveying devices to transport coal between components nor to return coal to the container from which it was sampled.

It is a further object of the present invention to provide a coal sampling device which will transport a final small sample of about 1–2 lbs. directly to the operator's compartment for identification and bagging.

Additional objects, advantages and other novel features of the invention will be set forth in part in the description that follows and in part will become apparent to those skilled in the art upon examination of the following or may be learned with the practice of the invention.

To achieve the foregoing and other objects, and in accordance with one aspect of the present invention, an improved coal sampling device is provided having an auger-type solid material core extractor which propels uncrushed pieces of coal from a container of coal to a separating device that allows most of these extracted coal pieces to fall back into the container through several open windows. The separating device also includes an additional window through which extracted coal pieces fall into a crushing device, where the coal pieces are crushed to pebble-sized pieces, useful for laboratory analysis. The crushed coal pieces are allowed to fall out of the bottom of the coal crushing device, and a portion of the crushed pieces are collected by a sample collecting receptacle, which accumulates portions of the crushed coal throughout the core extraction process so that a true representative sample of the total extracted core is collected by this receptacle. During the extraction/sampling process, or at the end thereof, the crushed coal sample is removed from the receptacle by a vacuum or air pressure which is provided to propel the crushed coal pieces through a hose or pipe that directs the crushed coal sample to a laboratory or collecting work station. Alternatively, the crushed coal could be removed from the sample collecting receptacle by other mechanical means, such as a conveyor belt.

By use of the preliminary separation procedure before crushing the core sample, the required crusher size is much smaller than would be required if the entire extracted core sample were to be crushed. This allows the overall coal sampling device to be much smaller in physical size, and it consumes much less electricity. In addition, the entire coal sampling device can be attached and supported by the end of a boom of a hydraulic lift. Such a hydraulic lift can be located on a trailer or a truck, thereby making the entire coal sampling device portable. A laboratory or collecting station can also be located on the same trailer so that the entire coal sampling device and laboratory or collecting work station are portable together in one assembly.

Still other objects of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

DETAILED DESCRIPTION OF THE PREFERRED EMBODIMENT

Reference will now be made in detail to the present preferred embodiment of the invention, an example of which is illustrated in the accompanying drawings, wherein like numerals indicate the same elements throughout the views.

Figures 1, 2:
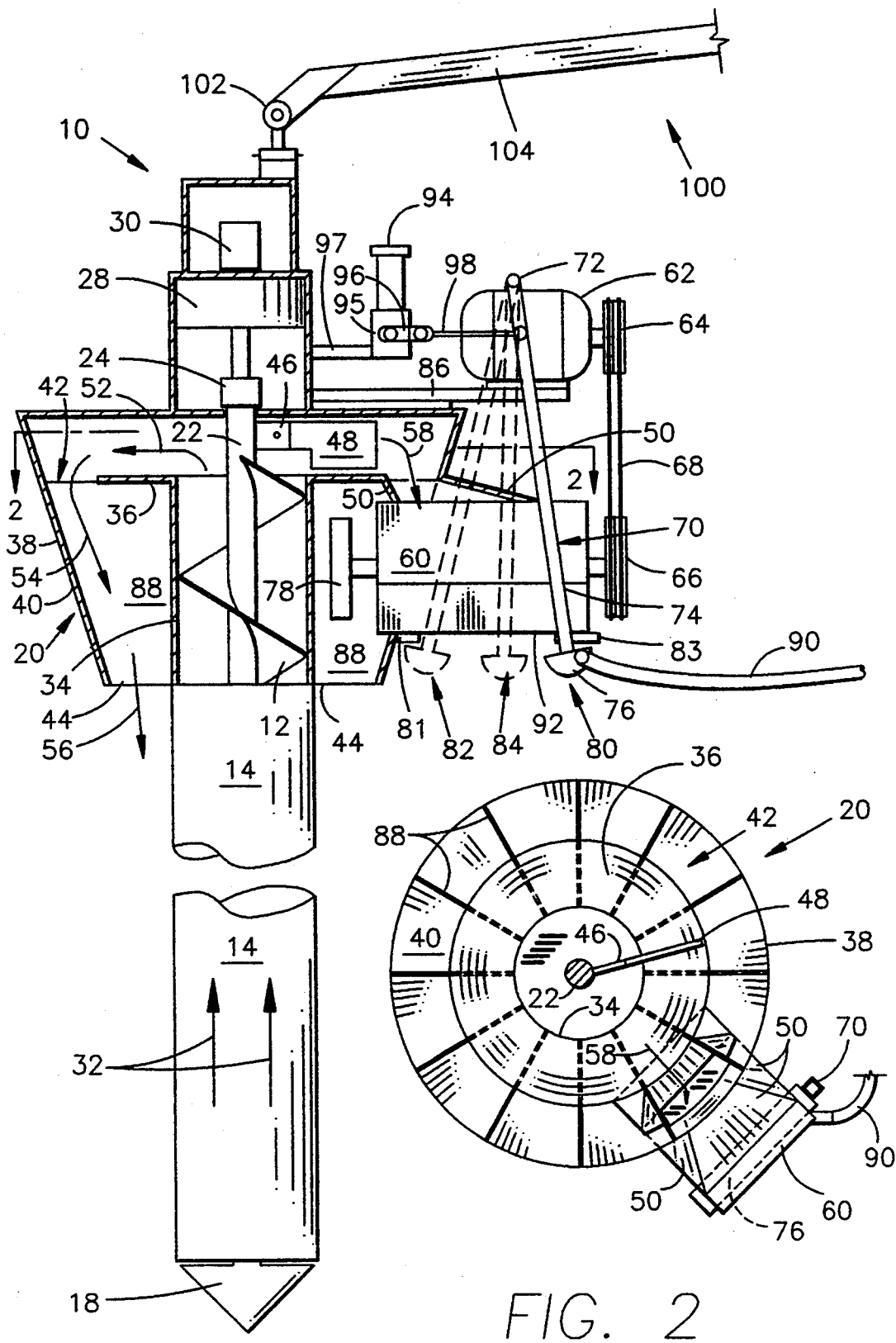
FIG. 1 is a partially cut-away side elevational view of a coal sampling device constructed in accordance with the principles of the present invention.
FIG. 2 is a partially cut-away top plan view of the coal sampling device of FIG. 1, taken along the line 2—2, showing the details of the separator device, excluding the boom and boom attachment points.

Referring now to the drawings, FIG. 1 shows a coal sampling device generally designated by the index numeral 10, suspended by a boom subassembly 100. Coal sampling device 10 includes a vertical blade auger 12 which turns inside an auger tube 14. An auger tip 18, which contains the teeth of the overall auger assembly, is located at the bottom portion of auger tube 14.

Adjacent to the uppermost portion of auger 12 is a separator subassembly 20, which is funnel shaped. The blade of auger 12 ends in the separator subassembly 20, however, the auger shaft 22 continues further up in the vertical direction to an auger drive coupling 24. Auger shaft 22 is propelled by a hydraulic motor 30, which preferably is manufactured by Commercial Intertech Company, located in Youngstown, Ohio, and has 65 horsepower and runs at 1050 RPM. The output of hydraulic motor 30 is connected to a planetary reduction gearbox 28, and its output is then connected to the auger drive coupling 24. The auger 12 preferably rotates at 175 RPM.

During operation, coal sampling device 10 is typically lowered into a container (not shown) of coal, such as a typical loaded coal truck. Coal sampling device 10 additionally could be easily used to extract coal from samples in railroad hopper cars or barges, or any other type of container which holds coal. It will be understood that coal sampling device 10 could also be used to extract and sample solid materials other than coal. It will additionally be understood that, as used throughout this patent, the word "coal" represents coal and its impurities, which may include a large quantity of rock material in a "coal" sample.

During use, coal sampling device 10 is lowered into the container holding the coal until the auger tip 18 reaches the top portion of the coal in that container. As auger 12 turns, coal is extracted from the container and the coal moves in the direction of arrows 32. Coal sampling device 10 is lowered throughout the majority of the vertical portion of the coal held in the container. In this way, a complete core sample is extracted from the coal held by the container.

As coal is extracted upward, along the direction indicated by arrows 32, it is contained by the outer wall 34 of the auger tube. Near the top of the auger blade 12, the outer wall 34 of the auger tube is bent outward at approximately a 90° angle to form a circular horizontal shelf 36, and to provide an outlet for the extracted coal moving up auger tube 14. Surrounding this portion of coal sampling device 10 is a tapered conical wall 40 of separator subassembly 20 which extends downward toward the auger tip 18. There are several openings or "windows" 42 near the top portion of separator subassembly 20. At the bottom-most portion of tapered conical wall 40 is another opening 44, which is also the bottom of separator subassembly 20.

A rotating arm 46 is attached to auger shaft 22, so that when the hydraulic motor 30 turns, auger 12 and the rotating arm 46 will turn at the same rate. A spreader bar 48 is attached to the outer diameter portion of rotating arm 46. As auger 12 turns, uncrushed pieces of coal which have traveled up auger tube 14 are pushed onto horizontal shelf 36, as indicated by direction arrow 52. Such coal pieces are not necessarily forced off of the horizontal shelf 36 immediately, however, when spreader bar 48 comes into contact with such pieces of coal, it tends to push those pieces of coal off horizontal shelf 36 and through the window 42, as indicated by the direction arrow 54. Such coal pieces then fall via gravity through the funnel-shaped separator subassembly 20 and are guided by the tapered conical wall portion 40 until they fall through the opening 44 at the bottom of the separator, as indicated by the direction arrow 56. In this manner, windows 42 and opening 44 act as discharge or return outlets to guide extracted coal back into its original container, if desired.

As is most easily viewed in FIG. 2, separator subassembly 20 is divided up into several pie-shaped sections, which are each divided by radial fins 88. In the illustrated embodiment, there are twelve radial fins 88, which divide separator subassembly 20 into eleven windows 42, plus one additional outlet duct 50, which directs coal into a crusher 60. Outlet duct 50 is shaped to allow coal pieces to be pushed by spreader bar 48 off horizontal shelf 36, and then to drop into the top portion of crusher 60, as indicated by direction arrows 58. In this manner, outlet duct 50 acts as a sampling outlet by directing extracted coal into crusher 60, for further processing and sampling.

Crusher 60 is powered by an electric motor 62, which sits on a horizontal support 86. The output shaft of motor 62 is connected to a pulley 64, which drives a second pulley 66 via a drive belt 68. Motor 62 is preferably manufactured by Reliance Electric Company, located in Cleveland, Ohio, and has 10 horsepower and runs at 1800 RPM. Crusher 60 is preferably a standard coal crushing unit having the model number "45", manufactured by Holmes Brothers, Inc. located in Danville, Ill. Pulley 66 is integrally connected to an input shaft which is part of crusher 60, as is a flywheel 78 on the opposite side of crusher 60. The coal pieces that enter crusher 60 along direction arrow 58 are continuously crushed into smaller particles until they are small enough to fit through holes in the bottom floor 92 of crusher 60. It is preferred that the size of the holes in crusher floor 92 be ⅜ inch (or 10 mm) in diameter, so that the coal must be crushed to pebble-sized pieces smaller than ⅜ inch (10 ram) in diameter before it can exit crusher 60 through the outlet or bottom floor 92.

The crushed coal merely falls back to the container, via the holes in the crusher floor 92, unless captured by a sampler subassembly 70. Sampler subassembly 70 includes a pivot 72, a pivotable, elongated arm 74, and a sample collecting receptacle or retainer 76 which is illustrated as a half-cylinder, open along its top side. Sample retainer 76 is movable about pivot 72 such that its end travel includes a first rest position 80 and a second rest position 82, and also intermediate moving positions 84, which are at mid-travel (as seen in FIG. 1). An electric motor/brake 94 provides the drive for moving sampler subassembly 70. Motor/brake 94 drives into a speed reducing gearbox 95, which preferably has a 40:1 gear ratio. A crankshaft 96 is mounted to the output shaft of speed reducer 95, and a connecting rod 98 is used to transmit a horizontal movement from crankshaft 96 to pivotable arm 74.

While sample retainer 76 is located in either rest position 80 or 82, it is not accumulating any coal particles which are falling out of the crusher floor 92. Such coal particles are accumulated only as sample retainer 76 is moving between rest positions 80 and 82, or in other words, while sample retainer 76 is in a moving, mid-travel position 84.

In the illustrated embodiment, auger 12 is twelve inches (305 mm) in diameter, but somewhat less than ten feet (10' = 3.0 m) in length. As the auger turns, the largest chunk of coal expected to come up its tube 14 would be approximately 6"×6"×6" (152 mm) in size. Therefore, the preferred size of the windows 42 is approximately 6"×6" (152 mm) so that even the largest chunk of coal can easily fall through one of the windows 42. In the illustrated embodiment of FIG. 1, most of the coal pieces can fall directly through the funnel-shaped separator subassembly 20, then out its bottom openings 44, and directly back into the original container of coal from which the original coal pieces came.

During the operation of coal sampling device 10, as it extracts coal from a fully loaded truck, for example, approximately 200–400 pounds of coal will be augured up auger tube 14 and captured into the separator subassembly 20. If all of this coal needed to be crushed in the short time period that is typically required by a coal production facility, then a much larger sampler typically requiring a 40 horsepower crusher would be required. However, coal sampling device 10 only crushes approximately one-twelfth of the coal extracted from the truck in the illustrated embodiment. Therefore, crusher 60 need only crush about forty pounds or less of coal during that same time period, and a much smaller crusher can be used, one requiring ten horsepower or less in size.

A forty pound crushed sample of coal is still much larger than is needed for laboratory analysis, which only requires about a one or two pound final sample. Therefore, sampler subassembly 70 need only capture approximately one or two pounds of the crushed coal out of the forty pounds or less of coal which is falling through the holes in the crusher floor 92. For this reason, it is preferred that the sample collecting receptacle or retainer 76 remain in one rest position 80, or the other 82, for the majority of the time as coal is being crushed by crusher 60. The preferred mode of operation of sampler subassembly 70 is to keep the sample retainer 76 in one of the rest positions for approximately three seconds at a time, then to sweep or "cut" underneath the crusher floor 92, while moving sample retainer 76 through its mid-travel position 84, within a time interval of about one second or less sweep time. In this way, the coal particles will be sampled throughout the operation of the auger 12 such that somewhat random samples of coal will be accumulated from start to finish. This will ensure that a representative sample of the core drilled by auger 12 will be accumulated for laboratory analysis. It is preferred that the sample retainer 76 make a minimum of six "secondary" cuts per each penetration of auger 12 into the coal container. In this way, the proper amount of crushed coal should be accumulated by sample retainer 76 at the end of the core extraction procedure.

In addition to the somewhat random sampling of sampler subassembly 70, the overall design of spreader bar 48, windows 42, and outlet duct 50 prevent an accidental or intentional bias by a system operator as to which coal pieces fall into crusher 60. A fairly representative sample of the overall core extracted by coal sampling device 10 will be accumulated in sample retainer 76.

Figure 3:
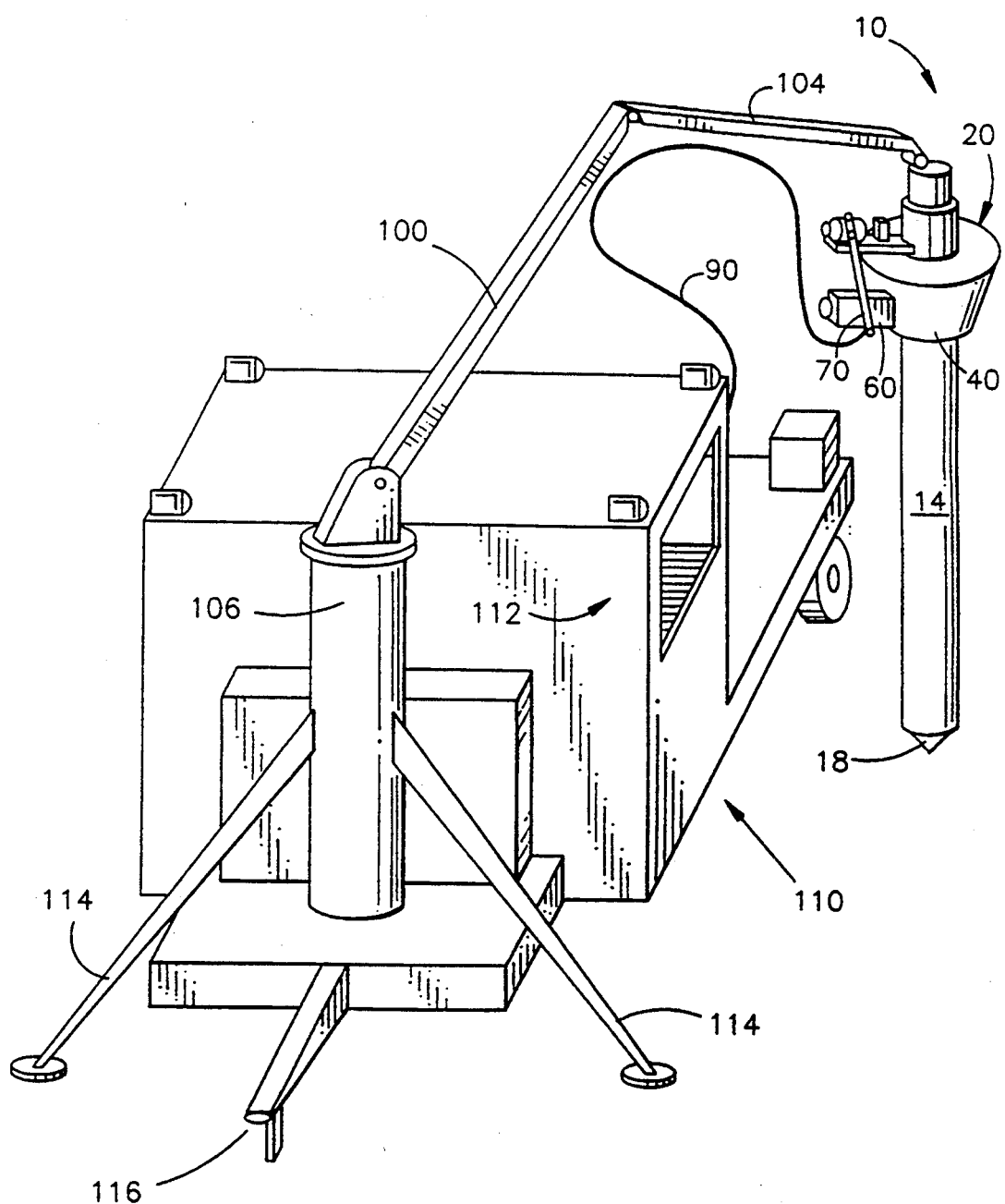
FIG. 3 is a perspective view of a trailer assembly that includes a hydraulic lift having a boom that supports the coal sampling device of FIG. 1.

For a given core extraction procedure, during and at the end of operation of coal sampling device 10, the coal particles that are accumulated in sample retainer 76 are removed through a hose 90 which leads to a receptacle bag (not shown) inside the operator's cab 112 (shown in FIG. 3). It is preferred that a vacuum source (not shown) be used to propel the coal particles from the sample retainer 76 into and through the air hose 90.

Figure 4:
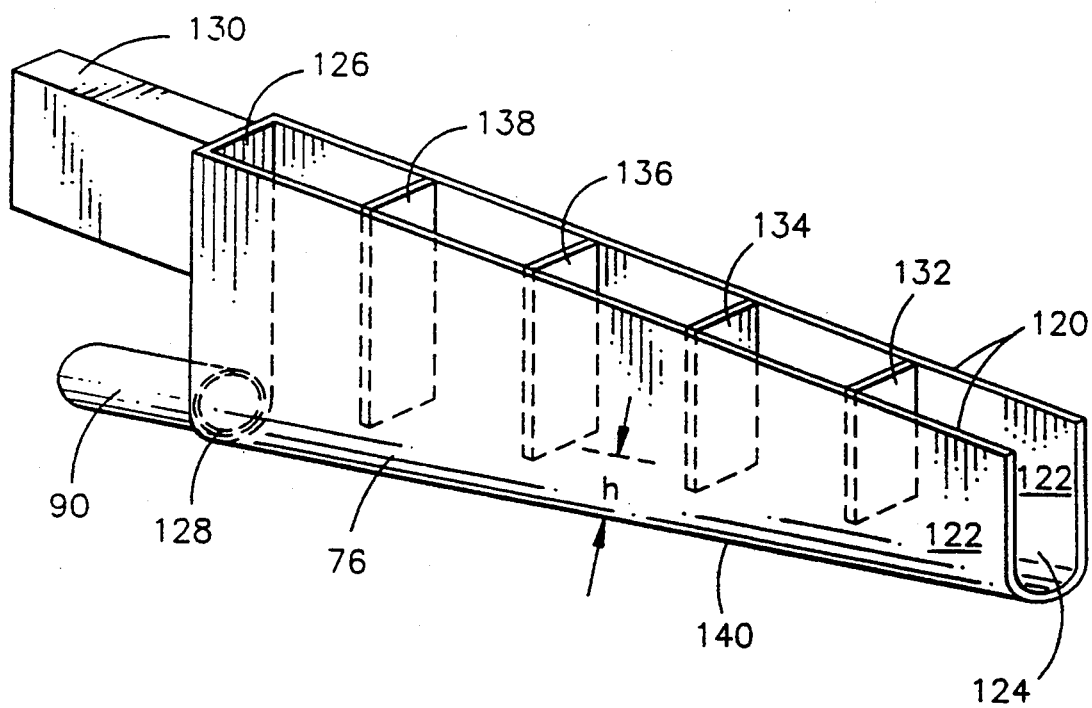
FIG. 4 is a perspective view of the sample retainer used in the coal sampling device of FIG. 1.

A rubber-like seal 81 is used to prevent atmospheric air from entering the top portions or edges 120 (see FIG. 4) of sample retainer 76 while in rest positions 82. Likewise, a rubber-like seal 83 is used to prevent atmospheric air from entering the top portions of sample retainer 76 while in rest position 80. As best viewed in FIG. 4, hose 90 is connected to a closed end 126 of sample retainer 76 by a hose connector 128. The opposite end 124 of sample retainer 76 is open to atmosphere, so that the vacuum source (not shown) can compel the coal particles to enter hose 90. The vacuum source is preferably a three (3) horsepower unit providing a vacuum of approximately sixty inches (60" = 1.52 m) of water at 180 CFM (cubic feet per minute).

The top edges 120 of sample retainer 76 are parallel to each other and preferably horizontal. The bottom portion 140 of sample retainer 76 is preferably sloped downward in the direction toward the air hose connection 128 at closed end 126. A mounting member 130 is provided for connecting sample retainer 76 to the pivotable arm 74. The dimensions of sample retainer 76 preferably are as follows: the horizontal distance from open end 124 to closed end 126 is about eighteen inches (18"=457 mm); the width between top edges 124 is about 1½ inches (1½"=38 mm), as is the width between vertical side walls 122; the vertical distance between top edges 124 and bottom portion 140, along open end 124, is about three inches (3"=76 mm); and the vertical distance between top edges 124 and bottom portion 140, along closed end 126, is about six inches (6"=152 mm).

Sample retainer 76 preferably contains a few baffles 132, 134, 136 and 138 to prevent atmospheric air from bypassing some of the coal particles. These baffles are of increasing length from the open end 124 (e.g., baffle 132) to the closed end 126 (e.g., baffle 138). The bottom edge of each baffle preferably provides a gap of about one inch (1"=25 mm) to the bottom portion 140 (see, for example, dimension "h" on FIG. 4). The baffles force the moving air to follow a path that is proximal to bottom portion 140, thereby removing most of the coal particles that are located along bottom portion 140. Without the baffles, the air flow could possibly follow a path that deviates from a close proximity to bottom portion 140, and which will not necessarily "sweep" most of the coal particles from bottom portion 140.

The coal particles are removed from sample retainer 76 and forced to enter hose 90 at time intervals that sample retainer 76 is in one or the other of rest positions 80 and 82. The rubber seals 81 or 83 close the top edges 120 from atmosphere, and air must flow through open end 124 into the hose 90. In this way, the coal sample is transported from sample retainer 76 into the receptacle bag without the use of any type of conveyer mechanism. However, it will be understood that a different style of sample retainer could be provided, and that crushed coal could be removed from that sample retainer by means other than a hose using air pressure or a vacuum.

It will be understood that coal sampling device 10 may be entirely suspended from and supported by the boom subassembly 100, and does not require any type of tower or framework as used in existing coal samplers. It will also be understood that the unused coal pieces that fall through the opening 44 at the bottom of separator subassembly 20 do not necessarily have to fall back into the container from which the coal pieces were extracted. Instead, such unused coal can be captured and retained at another location, if desirable.

FIG. 3 shows a trailer 110, preferably a twelve ton trailer, which contains operator's cab 112, and a hydraulic lift 106. Hydraulic lift 106 operates the boom subassembly 100, which includes a boom arm 104 that preferably has a twenty-two foot (22'=6.7 m) radius of operation. Boom 104 is connected to coal sampling device 10 via a two-way pivot 102 (as seen in FIG. 1). By use of this boom and hydraulic lift combination, coal sampling device 10 is readily shiftable in the vertical direction so as to be raised above a coal truck, then lowered into the load of coal within that truck. In addition, the boom arm 104 is readily shiftable in the horizontal direction throughout its twenty-two foot (6.7 m) radius so as to accommodate different positions of coal trucks as they approach the trailer 110.

Trailer 110 is stabilized by a pair of hydraulic stabilizers 114. Trailer 110 can be easily moved around by some type of vehicle such as a truck, and can be connected to that vehicle by a pintle hitch 116. By virtue of the fact that the trailer 110 can be moved by a motor vehicle, coal sampling device 10 truly is a portable device and can be used in several different applications, both at coal shipping and coal receiving stations. It will be understood that coal sampling device 10 may be attached to a permanent structure, such as a building, rather than being installed onto a portable apparatus. In addition, it could be permanently mounted onto a concrete pad. The word "portable" has been used throughout this patent as meaning that sampling device 10 is simply small enough in size and light enough in weight to be mounted to the end of a boom arm so that the entire device can be raised and lowered above a container of coal.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

We claim:
1. A coal sampling apparatus, comprising:
  (a) a coal extractor comprising an auger for extracting uncrushed coal from a container, thereby creating a primary coal sample, said coal extractor having an outlet through which the extracted coal is moved;
  (b) an integral coal separator for separating said primary coal sample received from the outlet of said coal extractor, said coal separator including a sampling outlet, through which a portion of said primary coal sample is directed, thereby creating a secondary coal sample that automatically exits said sampling outlet via gravity, said coal separator further including at least one discharge outlet that is open at its bottom portion thereby creating an open window through which the remaining portion of said primary coal sample automatically passes via gravity;
  (c) a coal crusher for crushing said secondary coal sample that passes through said sampling outlet into particles small enough for useful analysis thereby creating a crushed coal sample, said coal crusher having an outlet; and
  (d) a coal collector for collecting said crushed coal sample received from the outlet of said coal crusher, for analysis.

2. The coal sampling apparatus as recited in claim 1, wherein the uncrushed primary coal sample that passes through said at least one discharge outlet is directly returned to said container from which it was extracted.

3. The coal sampling apparatus as recited in claim 1, wherein the uncrushed primary coal sample that passes through said at least one discharge outlet is directly returned to said container from which it was extracted, and a portion of the crushed coal sample which is not collected for analysis by said coal crusher is directly returned to said container from which it was extracted.

4. The coal sampling apparatus as recited in claim 1, wherein said coal separator comprises a plurality of windows and a conical duct through which a majority of said uncrushed primary coal sample passes, said coal separator additionally having a window and a duct forming said sampling outlet through which said uncrushed secondary coal sample passes as it is transferred to said coal crusher.

5. The coal sampling apparatus as recited in claim 1, wherein said coal collector comprises an elongated arm, a support means, and a sample collecting receptacle, said arm having an upper end pivotally attached to said support means, said arm having a lower end terminating in said sample collecting receptacle, said arm being swingable to cause said sample collecting receptacle to periodically pass beneath the outlet of said coal crusher during operation of said coal sampling apparatus to obtain a representative coal sample.

6. The coal sampling apparatus as recited in claim 1, further comprising means for transporting the collected crushed coal to a collecting station.

7. The coal sampling apparatus as recited in claim 6, wherein said means for transporting the collected crushed coal sample to a collecting station comprises a hose through which an air pressure or vacuum is applied.

8. The coal sampling apparatus as recited in claim 1, wherein said apparatus is portable, and including a boom means for supporting and shifting said apparatus.

9. The portable coal sampling apparatus as recited in claim 8, wherein the uncrushed primary coal sample that passes through said at least one discharge outlet is directly returned to said container from which it was extracted.

10. The portable coal sampling apparatus as recited in claim 8, wherein said coal separator comprises a plurality of windows and a conical duct through which a majority of said uncrushed primary coal sample passes, said coal separator additionally having a window and a duct forming said sampling outlet through which said uncrushed secondary coal sample passes as it is transferred to said coal crusher.

11. The portable coal sampling apparatus as recited in claim 8, wherein said boom means and said coal collector comprise an elongated arm, a support means, and a sample collecting receptacle, said arm having an upper end pivotally attached to said support means, said arm having a lower end terminating in said sample collecting receptacle, said arm being swingable to cause said sample collecting receptacle to periodically pass beneath the outlet of said coal crusher during operation of said coal sampling apparatus to obtain a representative coal sample.

12. The portable coal sampling apparatus as recited in claim 8, further comprising means for transporting the collected crushed coal to a collecting station.

13. The portable coal sampling apparatus as recited in claim 12, wherein said means for transporting the collected crushed coal to a collecting station comprises a hose through which an air pressure or vacuum signal is applied.

14. A method of sampling coal, comprising the steps of:
(a) extracting uncrushed coal from a container by use of an auger, thereby creating a primary coal sample, and moving the uncrushed primary coal sample to an integral separating device;
(b) separating said uncrushed primary coal sample within said coal separating device by moving the coal through a plurality of outlets in said coal separating device, one of said outlets being a sampling outlet through which a portion of
(c) crushing said secondary coal sample that passes through said sampling outlet into particles small enough for useful analysis thereby creating a crushed coal sample; and
(d) collecting said crushed coal sample, for analysis.

15. The method of sampling coal as recited in claim 14, further comprising the step of directly returning, to said container from which it was extracted, the uncrushed primary coal sample that passes through said at least one discharge outlet.

16. The method of sampling coal as recited in claim 14, further comprising the step of directly returning, to said container from which it was extracted, the uncrushed primary coal sample that passes through said at least one discharge outlet and a portion of the crushed coal sample which is not collected for analysis.

17. The method of sampling coal as recited in claim 14, further comprising the step of transporting the collected crushed coal to a collecting station.

* * * * *

UNITED STATES PATENT AND TRADEMARK OFFICE
CERTIFICATE OF CORRECTION

PATENT NO. : 5,413,004
DATED : May 9, 1995
INVENTOR(S) : George F. Johnson, Jr.
Arnemann R. Gredner It is certified that error appears in the above-indentified patent and that said Letters Patent is hereby corrected as shown below:

Column 10, line 15 (claim 13), please delete the word "signal"

Column 10, line 27 (claim 14 (b)), after the word "of" insert:

--said primary coal sample is directed, thereby creating a secondary coal sample that automatically exits said sampling outlet via gravity, and at least one of said outlets being a discharge outlet that is open at its bottom portion thereby creating an open window through which the remaining portion of said coal sample automatically passes via gravity;--

Signed and Sealed this

Thirtieth Day of January, 1996

Attest:

BRUCE LEHMAN

Attesting Officer

Commissioner of Patents and Trademarks